United States Patent [19]
Hofmann et al.

[11] Patent Number: 5,810,837
[45] Date of Patent: Sep. 22, 1998

[54] DEVICE FOR THE IMPLANTATION OF A SELF-EXPANDING ENDOPROSTHESIS

[75] Inventors: Eugen Hofmann, Zurich; Marc Gianotti, Wiesendangen, both of Switzerland

[73] Assignee: Schneider (Europe) A.G., Bulach, Switzerland

[21] Appl. No.: 742,281

[22] Filed: Oct. 31, 1996

Related U.S. Application Data

[63] Continuation of Ser. No. 346,332, Nov. 29, 1994, abandoned, which is a continuation of Ser. No. 110,459, Aug. 23, 1993, abandoned.

[30] Foreign Application Priority Data

Dec. 16, 1992 [EP] European Pat. Off. .............. 92811008

[51] Int. Cl.⁶ .................................................. A61B 17/00
[52] U.S. Cl. ............................................................ 606/108
[58] Field of Search ............................................. 606/108

[56] References Cited

U.S. PATENT DOCUMENTS

| | | |
|---|---|---|
| 4,580,568 | 4/1986 | Gianturco . |
| 4,665,918 | 5/1987 | Garza et al. . |
| 4,681,110 | 7/1987 | Wiktor . |
| 4,732,152 | 3/1988 | Wallsten et al. . |
| 4,768,507 | 9/1988 | Fischell et al. . |
| 4,875,480 | 10/1989 | Imbert . |
| 5,026,377 | 6/1991 | Burton et al. . |
| 5,201,757 | 4/1993 | Heyn et al. . |
| 5,234,457 | 8/1993 | Andersen ............................ 606/108 X |

FOREIGN PATENT DOCUMENTS

| | | |
|---|---|---|
| 0416662 | 3/1991 | European Pat. Off. . |
| 0418677 | 3/1991 | European Pat. Off. . |

*Primary Examiner*—Michael H. Thaler
*Attorney, Agent, or Firm*—Peter C. Richardson; Lawrence C. Akers; Aaron Passman

[57] ABSTRACT

The endoprosthesis is inserted under tension in a recess of a flexible inner catheter and secured by means of a tube-shaped outer catheter. To release the endoprosthesis into a vessel, the outer catheter is pushed back over the recess. The recess is formed by a connector piece that connects a tip to a piece of tubing of the inner catheter. The inner catheter can be designed with a smaller outer diameter in the region of the recess than was previously the case with at least the same flexibility and resistance to buckling.

10 Claims, 4 Drawing Sheets

DEVICE FOR THE IMPLANTATION OF A SELF-EXPANDING ENDOPROSTHESIS

This a continuation of application Ser. No. 08/346,332, filed on Nov. 29, 1994, now abandoned, which is a continuation of application Ser. No. 08/110,459, filed on Aug. 23, 1993 now abandoned.

BACKGROUND OF THE INVENTION

The invention relates to a device for implanting a self-expanding endoprosthesis in a vessel, with a flexible, oblong outer catheter with a distal end and a proximal end and with a flexible, oblong inner catheter that is arranged coaxially with respect to the outer catheter and which has a tip at the distal end and proximally at the perimeter of this a recess for receiving the endoprosthesis, whereby in order to secure the endoprosthesis, the outer catheter can be slid lengthwise over the recess and can be drawn back in order to release the endoprosthesis into the vessel.

Self-expanding endoprostheses, which are inserted into the vessel to be treated by means of a device of the type mentioned above, have been used for some time for the treatment of occlusive arterial diseases. A well-known endoprosthesis is the Wallstent® endoprosthesis, which is made of tubular steel wire mesh. Endoprostheses of this type are frequently called "stents."

A well-known device for implanting these endoprostheses is manufactured by the applicant. The inner catheter of this device has a flexible tube that incorporates a recess on the outer side directly behind the distal tip. The endoprosthesis to be inserted into the vessel is slid into this recess. When the outer catheter is pulled back, the endoprosthesis rests proximally against a shoulder of this recess. The recess thus serves to receive the endoprosthesis and prevents it from shifting axially on the inner catheter when the outer catheter is drawn back. The endoprosthesis is fixed under tension by the outer catheter. By withdrawing the outer catheter, the endoprosthesis is released and, in the process, expands at the expense of its length to a predetermined outer diameter. Consequently, the endoprosthesis can rest against the inside of the vessel wall to be treated. After the endoprosthesis is released, the device is pulled out of the vessel. In practice, the operation of this device has proven to be simple, fast and safe. Similar catheters have become known via U.S. Patent A-5,026,377, European Patent A-0 416 662 and European Patent A-0 418 677.

Endoprostheses with comparatively large outer diameters are being implanted more and more as well. In order that these endoprostheses can exert the necessary supporting pressure on the vessel, they have, accordingly, a greater number of wires. At the same time, these wires are also thicker than is normally the case in smaller endoprostheses. Until now, in order to implant these comparatively large endoprostheses, devices with a correspondingly larger outer diameter had to be used. In particular, the recess in the inner catheter cannot be deepened by whatever amount in order to receive a larger endoprosthesis. If the recess is too sharply pronounced, the inner catheter would buckle in the region of the recess in winding stretches of a vessel. Previously, a larger outer diameter meant a larger puncture site, on the one hand, and less accessibility to narrower vessels, on the other, as well as difficult maneuverability, for example, when inserting the device in a side branch of a vessel. A device with a larger outer diameter puts considerably more stress on a patient than a device with a smaller outer diameter. On the one hand, the puncture site is correspondingly larger when the device has a larger outer diameter. The risk of complications after removal of the device becomes correspondingly greater. Poorer accessibility means a longer treatment period and as a result, greater stress on the patient as well. Greater stress on the patient also occurs because a device with a larger outer diameter severely hinders the flow of the vascular medium for the length of time the device is in the vessel. Thus it would be desirable to have a generic-type device that had a smaller outer diameter with the same endoprostheses. The device should nevertheless guarantee simple, fast and safe operation and be able to be manufactured inexpensively.

SUMMARY OF THE INVENTION

With a generic device, the problem is solved by the fact that the recess for receiving the endoprosthesis is formed from a connector piece on the inner catheter.

In the device according to the invention, there is a large degree of freedom in the choice of material, dimensions and manufacturing method for the connector piece. Thus, for example, no special requirements are placed on the connector piece with respect to antifriction properties and transmission of tractive force other than those placed on the rest of the inner catheter. The material, dimensions and manufacturing method used in making the connector piece therefore are not dependent on these properties. On the other hand, the material, dimensions and manufacturing method used for the main section of the inner catheter shaft can be selected in such a way that these properties are especially pronounced. In the area of the recess, the inner catheter can be designed with a smaller outer diameter with at least the same flexibility and resistance to buckling. Outside the recess, the inner catheter can have, for example, a larger inner diameter, regardless of the size of the recess, in order to achieve greater flexibility of the catheter shaft. A smaller outer diameter in the region of the recess means increased volume for receiving the endoprosthesis. With the same inner diameter of the outer catheter and with the same axial extension of the recess, more room is available to house the endoprosthesis in the device according to the invention. Thus with the same inner diameter of the outer catheter, a larger endoprosthesis can be mounted. Without increasing the stress on the patient, more and better treatment methods are thus available, i.e., treatment with larger endoprostheses, treatment with better tolerated endoprostheses the individual wires or fibers of which, for example, are coated, treatment with endoprostheses with greater expansive force, or treatment with endoprostheses that are supposed to prevent the growth of tumors in the vessel by means of a tube-shaped casing. The device can also be manufactured inexpensively. The high manufacturing cost necessary to obtain the required properties in the region of the recess does not extend to the entire length of the device, but rather remains limited basically to the length of the recess. For the remaining length of the inner catheter, then, relatively simple raw material can be used.

It now turns out, surprisingly, that the device according to the invention is considerably easier to use with respect to mounting the endoprostheses than the previously known device. Since, as has been mentioned above, more room is available to house the endoprosthesis with the same outer diameter, it is also considerably easier to mount the endoprosthesis. Since previously it was necessary to use a special device to mount the endoprosthesis, it is now possible with the device according to the invention to mount the endoprosthesis by hand. In practice, this means that the endoprosthesis does not have to be mounted in advance as before, but rather can be mounted immediately prior to using the device. In the process, the endoprosthesis can be cut to the desired length from a longer piece. On the one hand, this prevents the endoprosthesis from having to be sterilized under tension, prevents it from losing tension as a result of being stored for a long time under tension, and, on the other hand, prevents the physician from having to mount, store, and keep available a greater number of devices with endoprostheses of different lengths.

The connector piece is reinforced according to a further development. For example, this can result from a suitable design, for example, by means of ribs on the outside or, for example, via a type of sheathing on the connector piece. A connector piece made out of a composite material is especially suited. Connector pieces that are reinforced by means of fibers, particularly glass fibers, or that are made, at least in part, of metal are also suitable.

As a rule, it is sufficient if the connector piece is basically the length of the recess. The connector piece can thus be comparatively short, so that even if expensive raw materials are used in manufacturing the connector piece, they do not have a considerable impact on the manufacturing costs of the device. Additional advantageous properties become evident from the conditional claims, the following description, and the drawing.

BRIEF DESCRIPTION OF THE DRAWINGS

Examples of the invention's design are explained in the following by means of the drawing. It shows.

DETAILED DESCRIPTION OF THE INVENTION

Figure 1:
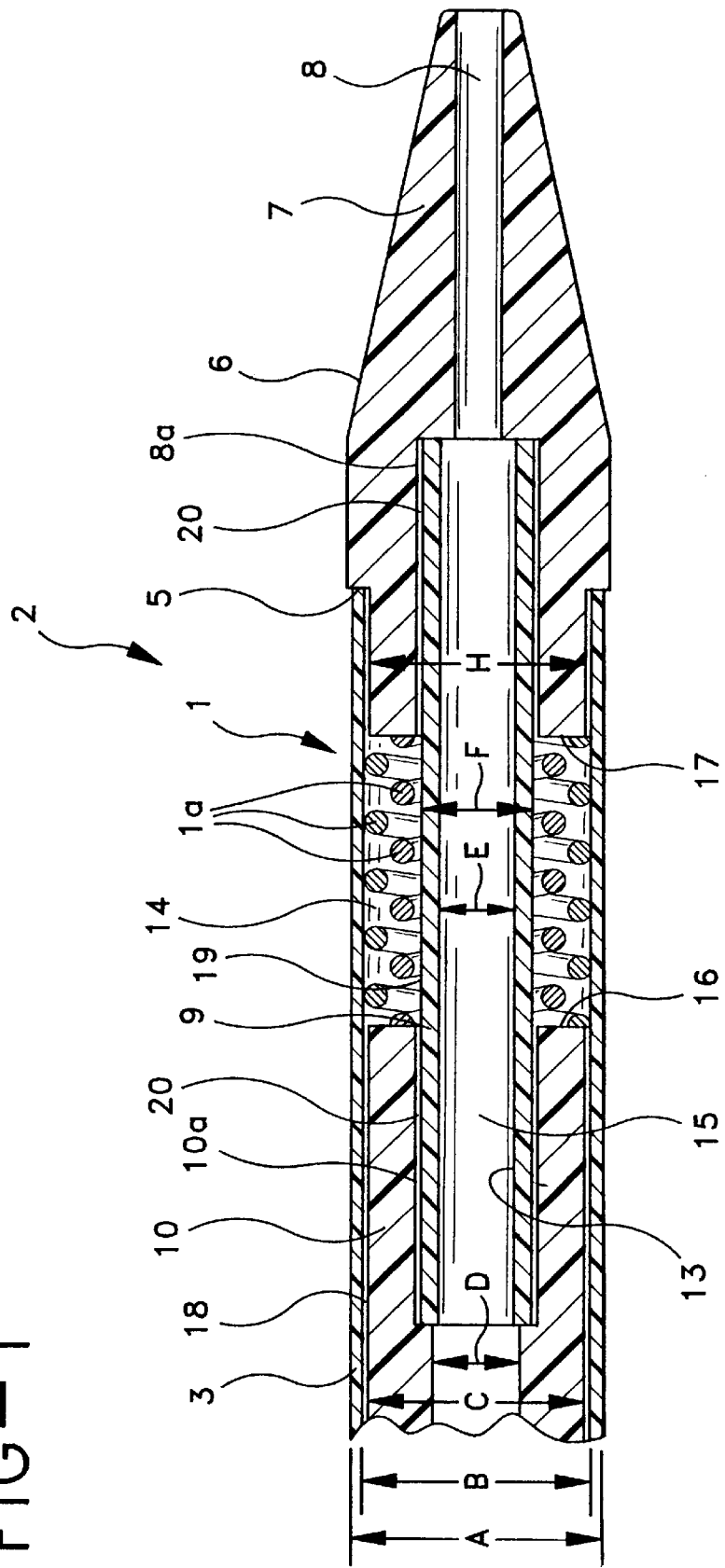
FIG. 1 a longitudinal section through the distal end of a device according to the invention, FIG. 2 the distal end according to FIG. 1, inserted in a vessel and with a partially released prosthesis, FIG. 3 the distal end of a variation of the device according to the invention, also in longitudinal section, and FIG. 4 a partial cutaway view of a device according to the invention.

FIG. 1 shows an endoprosthesis 1 that is mounted in a device 2 according to the invention. Endoprosthesis 1 is made of stainless steel wires 1a and can be fitted on the outside with an expandable casing, which is not shown here. Over the radially tensed endoprosthesis 1 is pushed an outer catheter 3, which is basically a flexible, oblong tube with a distal opening 5. Endoprosthesis 1 rests against the inside of the outer catheter. Outer catheter 3 prevents endoprosthesis 1 from expanding radially. Both endoprosthesis 1 and outer catheter 3 are in themselves known to the expert.

An inner catheter 6 is inserted into outer catheter 3 through opening 5. This inner catheter 6, which is also oblong and flexible, can have a continuous lumen 15 for receiving a guide wire, which is in itself known. However, a model with no inner lumen 15 is also possible. In this case, a guide wire, which is not shown here, cannot be attached at the distal end of inner catheter 6. As is evident from FIG. 1, inner catheter 6 has a tip 7, a connector piece 9, and a piece of tubing 10, which is arranged proximally with respect to connector piece 9. Connector piece 9 is cylindrical on the outside and has an outer diameter F, which is smaller than outer diameter C of tubing piece 10 and also smaller than outer diameter H of tip 7. Outer diameters C and H are essentially the same and are only slightly smaller than diameter B of the cylindrical interior 18 of outer catheter 3. Cross-sectional areas 16 and 17 of tubing piece 10 and tip 7, which are spaced a distance from one another, as well as interior 18 of outer catheter 3 and cylindrical exterior 19 of connector piece 9, form a hollow cylindrical space 14 in which mounted endoprosthesis 1 is housed. The distance between areas 16 and 17 is essentially given by the length of endoprosthesis 1 in its mounted state.

Figure 3:
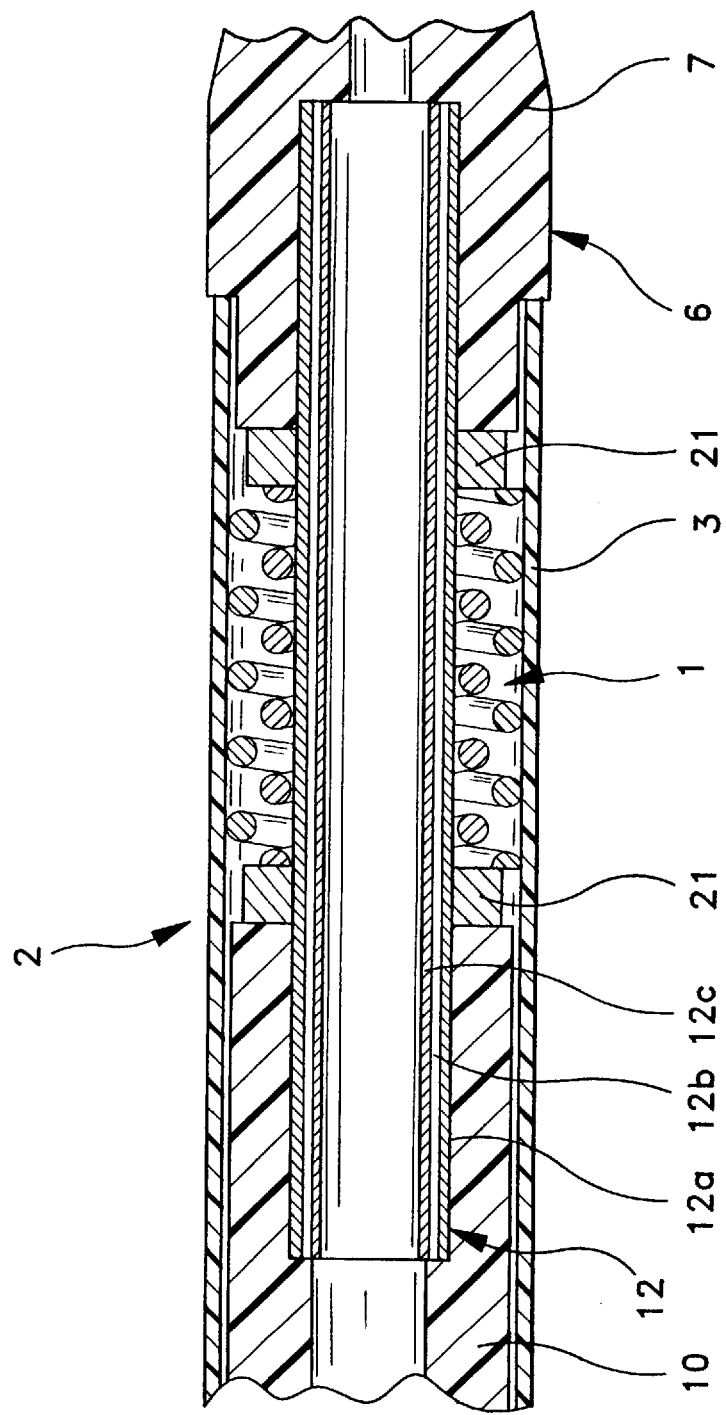

As is evident, connector piece 9 is somewhat longer than the distance between areas 16 and 17, with one end inserted in an enlarged slot boa in tubing piece 10 and the other end in an enlarged slot 8a of tip 7. These ends are securely connected to tubing piece 10 and tip 7 with, for example, a suitable adhesive 20. Other connections are also conceivable here, for example, by welding connector piece 9 to tubing piece 10 and tip 7. Connector piece 9 can be made of a material that is just as flexible and buckle-resistant with a smaller outer diameter F as the raw material of tubing piece 10. A reinforced raw material, for example, is suitable for this. Moreover, connector piece 9 can be made of a composite material, for example. In this regard, FIG. 3 shows a connector piece 12 that is made up of coaxial layers 12a, 12b and 12c. These composite materials are in themselves known. Connector piece 9 can be reinforced by means of fibers, in particular, glass fibers. A model in which connector piece 9 is also reinforced with a metal insert is conceivable as well. Such a connector piece is at the same time both flexible and buckle-resistant with a comparatively small outer diameter F, as is required for inner catheter 6, particularly in the distal region, especially if endoprosthesis 1 is to be inserted in a winding section of a vessel. Obviously, essentially the entire length of outer catheter 3, and with it all of device 2, is also flexible. The aforementioned reinforcement of connector pieces 9 and 12 guarantees that inner catheter 6 is buckle-resistant in the region of endoprosthesis 1, as required.

Figure 4:
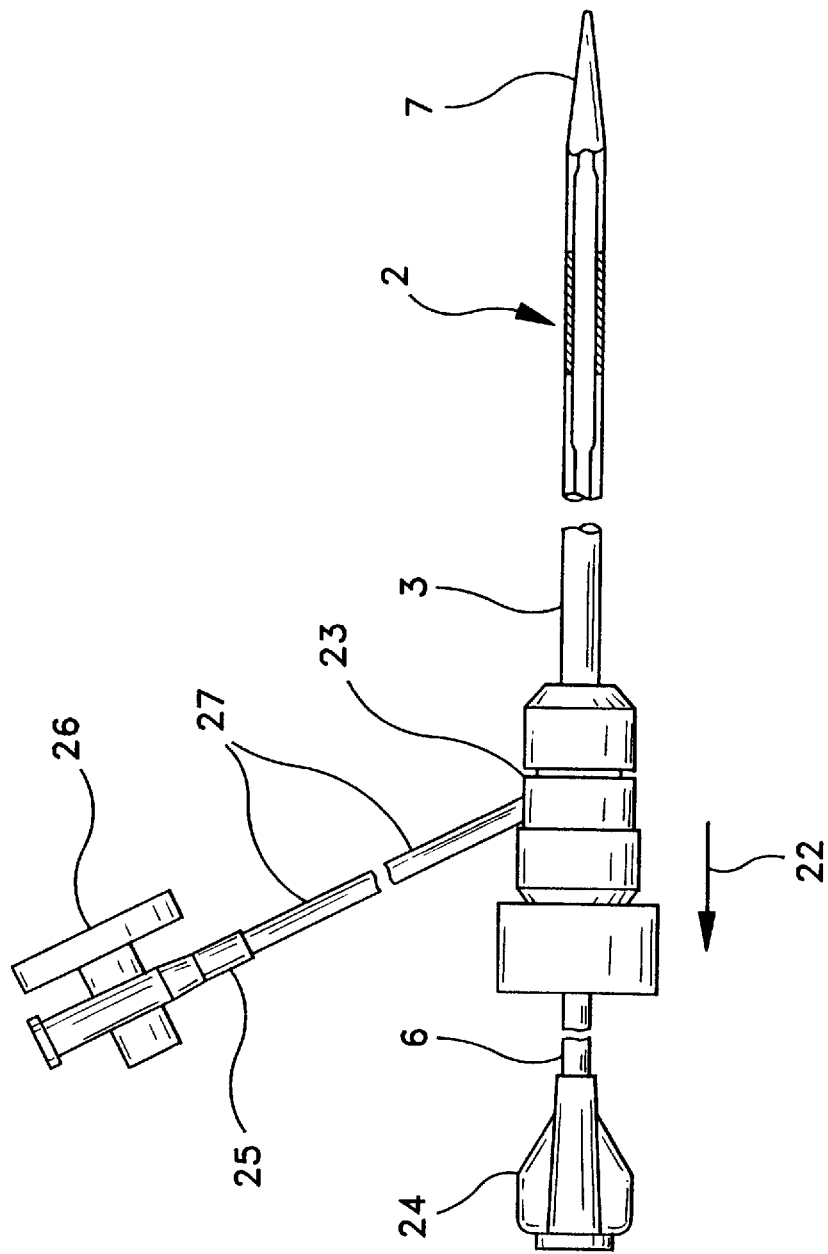

A suitable device 2 for inserting endoprosthesis 1 with an outer diameter of up to 40 mm slack has, for example, the following dimensions: A=5.2 mm, B=4.6 mm, C=4.5 mm, D=1.8 mm, F=2.00 mm, E=1.6 mm, and H=4.53 mm. The difference between the diameters of areas 18 and 19 is thus 2.25 mm. This difference is large enough for mounting an encased endoprosthesis with an outer diameter of up to 25 mm slack or an uncoated endoprosthesis with an outer diameter of up to 40 mm slack. In this case, outer catheter 3 is made of tetrafluoroethylene, and both tubing piece 10 as well as tip 7 are made of polyurethane. As a rule, marker rings 21 made of gold or tantalum are fitted on connector piece 9. These marker rings are shown in FIG. 3. As FIG. 3 indicates, rings 21 can form shoulders against which the mounted endoprosthesis rests. The use of device 2 is explained briefly in the following using FIG. 2 and 4.

Figure 2:
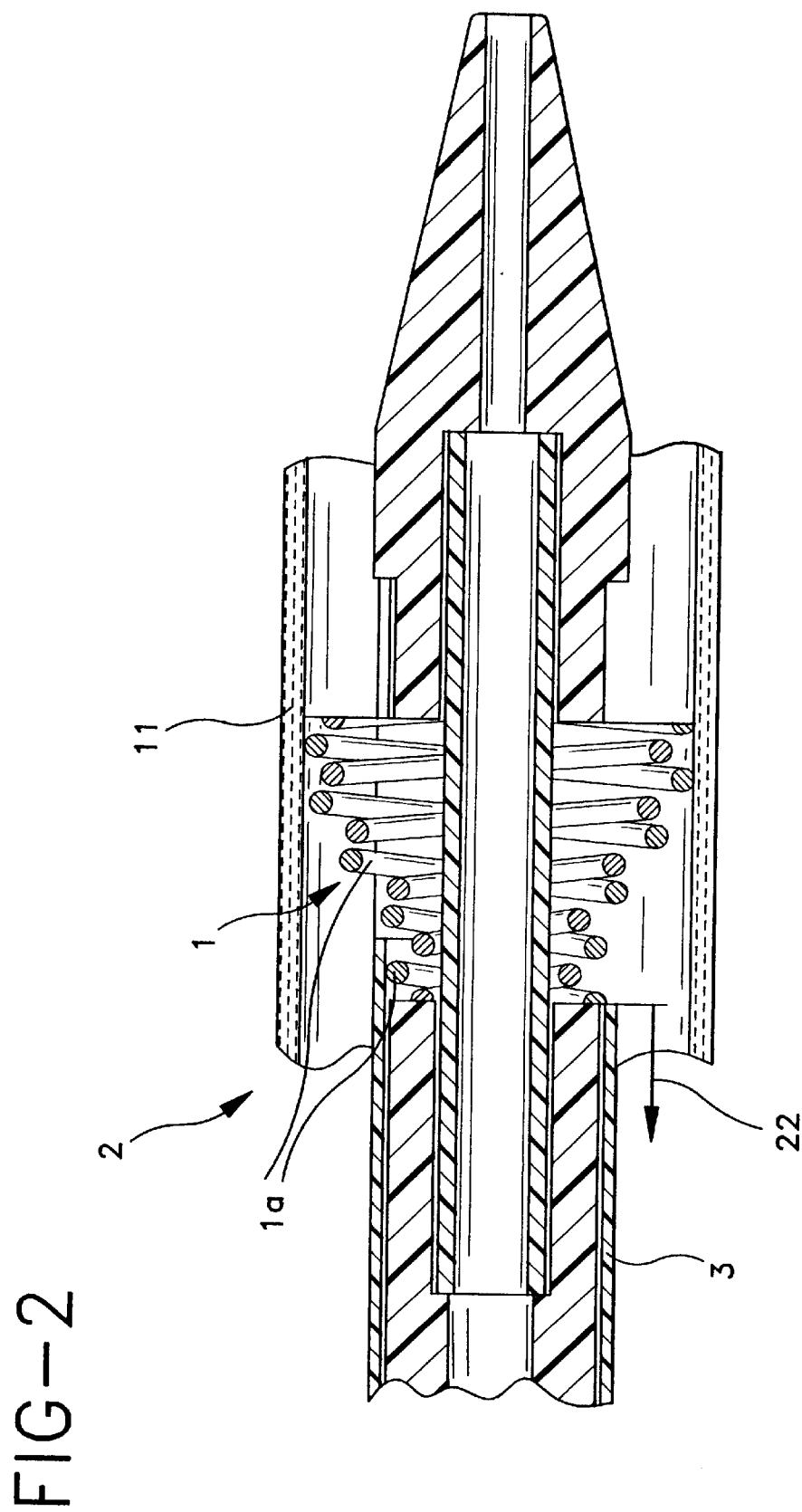

Reference number 11 designates a vascular wall of, for example, a blood vessel that has been expanded beforehand with a balloon catheter, for instance. In order to stabilize this enlargement with endoprosthesis 1, the distal end of device 2 is inserted in the vessel over an insertion lock, which is in itself known and which is not shown, until endoprosthesis 1 is advanced to the appropriate site. In this case, endoprosthesis 2 is fixed by outer catheter 3. By pulling back outer catheter 3 in the direction of arrow 22 to a joining and sealing piece 23 that is securely connected to this, endoprosthesis 1 is gradually released, as is shown in FIG. 2. In so doing, inner catheter 6 is at the same time held firmly at its proximal end, which has a connecting piece 24 for injecting contrast media and inserting a guide wire. Endoprosthesis 1 is released as soon as opening 5 of outer catheter 3 is pulled back across area 16 of tubing piece 10. The entire length of endoprosthesis 1 now rests against the interior of vascular wall 11 with a specific supporting pressure. Device 2 is now completely withdrawn, leaving endoprosthesis 1 in the vessel. If necessary, several endoprostheses can be placed one behind the other and together with one another in this manner.

As has already been mentioned above, endoprosthesis 1 is to be mounted immediately prior to using device 2. In the process, endoprosthesis 1 is cut to a suitable length from a longer piece. By pulling back outer catheter 3 partially, endoprosthesis 2 is then tensed by hand and inserted in recess 14. At the same time, outer catheter 3 is moved across endoprosthesis 1 in the opposite direction to arrow 22 up to the stop on tip 7. Device 2 can now be used. A suitable agent can be injected as needed through lumen 15 and a bore hole 8 of tip 7 by means of a branch line 25 with a stopcock 26 and a flexible hose line 27.

We claim:

1. A device for implanting a self-expanding endoprosthesis in a vessel, comprising:
   (a) a hollow outer tubular member having a distal end, a proximal end, a longitudinal length, and a constant inside diameter;
   (b) a one piece inner tubular member having a distal end and a proximal end and a constant outer diameter therebetween which is slightly smaller than the outer tubular member inside diameter, the inner tubular member coaxially arranged inside the hollow outer tubular member for relative longitudinal movement with respect to the hollow outer tubular member and extending substantially along the entire longitudinal length of the outer tubular member, the inner tubular member defining a first slot at its distal end;
   (c) a connector member having a distal end and a proximal end, with the proximal end inserted into the first slot of the inner tubular member; and
   (d) a tip with a proximal end defining a second slot therein inserted over the distal end of the connector member and further defining a recess with the connector member and the inner tubular member for receiving a self-expanding endoprosthesis.

2. The device according to claim 1 wherein the distal end of the connector member is secured in the second slot by means of an adhesive.

3. The device according to claim 1 wherein the proximal end of the connector member is secured in the first slot by means of an adhesive.

4. The device according to claim 1 wherein two marker rings are fitted on the connector member at a distance axially spaced from one another and which protrude radially from the connector member to secure an endoprosthesis inserted over the connector member distally and proximally so the endoprosthesis does not shift axially along the connector member.

5. The device according to claim 1 wherein the connector member has an outer diameter of approximately 2.3 mm and the inner tubular member has an outer diameter of approximately 4.5 mm.

6. The device according to claim 1 wherein the connector member is hollow.

7. The device according to claim 6 wherein the connector member has an inner passageway with a first inner diameter and wherein the inner tubular member has a second inner passageway with a second inner diameter that is greater than the first inner diameter.

8. The device according to claim 7 wherein the first inner diameter is approximately 1.6 mm and the second inner diameter is approximately 1.8 mm.

9. The device according to claim 1 wherein the inner tubular member is made of polyurethane.

10. The device according to claim 1 wherein the tip is made of polyurethane. This is a continuation, of application Ser. No. 08/346,332, filed on Nov. 29, 1994, now abandoned which is a continuation of application Ser. No. 08/110,459, filed on Aug. 23, 1993, now abandoned.

* * * * *